US012796906B2

(12) United States Patent
Tian et al.

(10) Patent No.: US 12,796,906 B2
(45) Date of Patent: Nov. 17, 2026

(54) OCULAR PARAMETER EVALUATION APPARATUS

(71) Applicant: SHANGHAI BAIYI HEALTHCARE TECHNOLOGY CO., LTD., Shanghai (CN)

(72) Inventors: Chaonan Tian, Shanghai (CN); Dong Du, Shanghai (CN)

(73) Assignee: SHANGHAI BAIYI HEALTHCARE TECHNOLOGY CO., LTD., Shanghai (CN)

( * ) Notice: Subject to any disclaimer, the term of this patent is extended or adjusted under 35 U.S.C. 154(b) by 155 days.

(21) Appl. No.: 19/053,405

(22) Filed: Feb. 13, 2025

(65) Prior Publication Data

US 2025/0176820 A1 Jun. 5, 2025

Related U.S. Application Data

(63) Continuation of application No. PCT/CN2022/132091, filed on Nov. 15, 2022.

(30) Foreign Application Priority Data

Aug. 18, 2022 (CN) ........................ 202210989498.3

(51) Int. Cl.
*A61B 3/00* (2006.01)

(52) U.S. Cl.
CPC ................................. *A61B 3/0025* (2013.01)

(58) Field of Classification Search
CPC ....... A61B 3/0025; A61B 3/00; A61B 3/0008; A61B 3/0033; A61B 3/0075;
(Continued)

(56) References Cited

U.S. PATENT DOCUMENTS 5,379,079 A 1/1995 Kratky
7,384,147 B1 * 6/2008 Ameri ..................... A61B 3/00 351/200

(Continued)

FOREIGN PATENT DOCUMENTS

CN 104116494 A 10/2014
CN 110215185 A 9/2019

(Continued)

OTHER PUBLICATIONS

Computer translation of CN113749606A (Year: 2021).*

(Continued)

*Primary Examiner* — Balram T Parbadia
*Assistant Examiner* — John C Sipes
(74) *Attorney, Agent, or Firm* — Central California IP Group, P.C.; Andrew D. Fortney

(57) ABSTRACT

An ocular parameter evaluation apparatus is disclosed, including a measurement unit and a human-computer interaction unit. the measurement unit and the human-computer interaction unit are on a base. The measurement unit includes at least one camera module, at least one canthal positioning arm, and a light source module. The camera module collects data of the eyes. The human-computer interaction unit adjusts position(s) of the canthal positioning arm(s) at the lateral canthus of the eye(s). The canthal positioning arm(s) are connected to obliquely-arranged mirrors. The light source module includes discretely distributed light bars and a near-infrared light source. The near-infrared light source is selectively coordinated with the light bars to assist the camera module in operation. When the apparatus is used as an exophthalmos examination device, the operation is simple and easy. After localization at the lateral canthus, measurement can include simply recording a video or taking an image.

17 Claims, 5 Drawing Sheets

(58) Field of Classification Search
CPC ....... A61B 3/0083; A61B 3/112; A61B 3/113; A61B 3/14; A61B 3/145; A61B 3/1005
See application file for complete search history.

(56) References Cited

U.S. PATENT DOCUMENTS

| | | | | |
|---|---|---|---|---|
| 2008/0151190 | A1* | 6/2008 | Bentley | A61B 3/135 351/211 |
| 2010/0152565 | A1* | 6/2010 | Thomas | A61B 3/16 600/405 |
| 2019/0287309 | A1* | 9/2019 | Samec | A61B 3/09 |
| 2020/0174345 | A1* | 6/2020 | Fujiki | H04N 23/60 |
| 2021/0386285 | A1* | 12/2021 | Walsh | A61B 3/18 |

FOREIGN PATENT DOCUMENTS

| | | | | | |
|---|---|---|---|---|---|
| CN | 112315424 | A | | 2/2021 | |
| CN | 113749606 | A | * | 12/2021 | A61B 3/14 |
| CN | 114305318 | A | * | 4/2022 | |
| CN | 114391805 | A | * | 4/2022 | A61B 3/0091 |
| WO | 2020235939 | A | | 11/2020 | |

OTHER PUBLICATIONS

Computer translation of CN114305318A (Year: 2022).*
Computer translation of CN114391805A (Year: 2022).*
International Search Report, International Appl. No. PCT/CN2022/132091, May 16, 2023.

* cited by examiner

OCULAR PARAMETER EVALUATION APPARATUS

CROSS-REFERENCE TO RELATED APPLICATIONS

This application is a continuation of International Pat. Appl. No. PCT/CN2022/132091, filed on Nov. 15, 2022, which claims priority to Chinese Pat. Appl. No. 202210989498.3, filed on Aug. 18, 2022, the contents of each of which are incorporated by reference herein in their entireties.

TECHNICAL FIELD

The invention relates to the technical field of measuring instruments, in particular to an ocular parameter evaluation apparatus.

BACKGROUND DISCUSSION

The measurement of ocular characteristic parameters is of great significance for medical treatment and scientific research. In practice, staff often need to obtain the characteristic parameters such as the eyeball exophthalmia and the palpebral fissure width of the tested person. At present, the commonly used measuring instruments include Hertel eyeball exophthalmia meters and CT scanners. The former requires manual operation and reading by the staff, and the differences in operating habits or using experience between the individual operators will lead to variability in the measurement results. Although the latter has high measurement accuracy, CT equipment has many problems, such as large radiation doses, high measurement cost and slow result generation. There is other, similar measuring equipment in related technology, but such equipment has many problems, such as complicated use and low measurement accuracy. Also, the devices mentioned in the background technology often cannot measure multiple eye parameters cheaply with the same device. That is, the equipment in the related technology is often only able to measure a single parameter, and a lack of high-precision data processing can result in poor measurement results, and cannot meet the user's measurement needs.

SUMMARY

In order to overcome the problems of high equipment cost, variability of measurement results and inability to use the same instrument to measure multiple parameters at a low cost in the related technology, the invention provides an ocular parameter evaluation apparatus to solve at least one problem in the related technology.

To achieve the above purpose, an ocular parameter evaluation apparatus is disclosed according to one aspect of the embodiment of the invention, which comprises:

A measurement unit and a human-computer interaction unit, wherein the measurement unit and the human-computer interaction unit are both configured on a base;

The measurement unit comprises at least one camera module, at least one canthal positioning arm, and a light source module, wherein the camera module is configured to collect data of one or more eyes;

The human-computer interaction unit adjusts the positions of the canthal positioning arm(s), so that the canthal positioning arm(s) are localized at a lateral canthus of the eye(s); the canthal positioning arm(s) are connected to obliquely-arranged mirrors, allowing the camera module to capture a side view virtual image video of the eye(s) from the mirrors;

The light source module comprises a plurality of light bars discretely distributed and a near-infrared light source; the near-infrared light source is selectively coordinated with the light bars to assist the camera module in operation; and After the near-infrared light source is turned on, the lighting sequence of the light bars is controlled successively to illuminate the light bars at different positions on the surface of the eye, and the camera module is synchronously controlled to collect the virtual image video stream of the one or more eyes in the mirror. The human-computer interaction unit intercepts the image frame corresponding to the reflected light with the longest visible light column appearing on the one or more eyes in the virtual image video stream, and obtains the ocular prominence value by analyzing the data of the intercepted image frame.

In an optional embodiment, the evaluation apparatus also comprises a control unit, which obtains instruction(s) received by the human-computer interaction unit to control the movement of canthal positioning arm(s) and position the canthal positioning arm(s) against the lateral canthus of the eye(s).

In another optional embodiment, the light bars and the near-infrared light source are electrically connected with the control unit, wherein:

The near-infrared light source is selectively coordinated with the light bars, wherein: the control unit controls the light bars to start in a predetermined order according to different measurement modes, or controls the start of the near-infrared (NIR) light source, or controls the light bars to start in a predetermined sequence and the NIR light source to start.

In another embodiment, the camera module is electrically connected to the control unit, wherein:

In response to an opening state of the light bars or near-infrared light source, the control unit controls the camera module to collect the eye video stream in the mirror according to the different measurement modes, or controls the camera module to collect a first gaze position image, a second gaze position image or a third gaze position image, or controls the camera module to collect the eve rotation state video stream.

In one embodiment, the measurement modes are at least one of the following measurement modes: eyeball exophthalmia, eye motion, palpebral fissure width, or conjunctival congestion.

In another embodiment, a wavelength of the near-infrared light source is 700-1200 nm.

In one embodiment, the evaluation apparatus further comprises a head rest and a jaw rest, wherein:

The head rest is connected with a horizontal moving platform, and the control unit is electrically connected with the horizontal moving platform to adjust front-and-back positions of the head rest; and The jaw rest is connected with a vertical moving platform, and the control unit is electrically connected with the vertical moving platform to adjust the up-and-down positions of the jaw rest.

In another embodiment, the number of the canthal positioning arms and the number of mirrors are both two, and are respectively configured on the left and right sides of the measuring unit. The mirrors are configured to tilt on the canthal positioning arms to form a virtual image corresponding to the eye in the mirror.

In other embodiments, the camera module comprises two area array cameras configured at its left and right sides, and/or the number of near-infrared light sources is two, and they are distributed on both sides of the measuring unit.

In another embodiment, the base has a card slot and/or multiple types of communication interfaces.

The technical scheme of the invention has the following advantages or beneficial effects:

(1) By integrating at least one camera module, at least one canthal positioning arm and a light source module in the measurement unit, the camera module is used to collect eye data. The human-computer interaction unit adjusts the position of the canthal positioning arm(s) so that the canthal positioning arm(s) are positioned at the lateral canthi of the eye(s). The canthal positioning arm(s) are connected to a tiltable mirror. The near-infrared light source selectively cooperates with the light bars to assist the work of the camera module. The apparatus in one embodiment is easy to operate. After the outer canthal positioning arm(s) are located, the measurement can be completed simply by taking video or images, and the eye parameters can be obtained by combining image recognition, which greatly improves the measurement efficiency and data measurement accuracy. It solves the problems of high measurement cost, low measurement efficiency and inability to measure multiple data synchronously, and the measurement equipment has no side effects such as radiation. The evaluation device of the invention can provide rich light field conditions, and then meet the measurement of multiple parameters, so that the evaluation device can be applied to a variety of measurement modes at low cost to obtain rich measurement data. The combination of the near-infrared light source and the light bars can produce a clear image of the reflected light of the eye contour in the mirror, so that the camera module can collect a clear exophthalmic video stream, improve the quality of the data source for image processing, and obtain an accurate measurement of the exophthalmic value. When the apparatus of the invention is used in an eye examination instrument, the measurement data has high precision, the measurement results have good stability, and the data measurement is no longer dependent on the user's experience.

(2) By using a near-infrared light field, the boundaries of the sclera, the iris and the pupil can be well distinguished, so that the accuracy and stability of the algorithm can be better improved. Therefore, the wavelength of near-infrared light source is 700-1200 nm, which can significantly improve the measurement accuracy of ocular prominence, eye motion or fissure width.

(3) The head rest is connected with a horizontal moving platform, and the control unit is electrically connected with the horizontal moving platform to adjust the front and back positions of the head rest. The jaw rest is connected with a vertical moving platform, and the control unit is electrically connected with the vertical moving platform to adjust the upper and lower positions of the jaw rest. At the same time, with the adjustment structure of canthal positioning arm(s), the positioning of the canthal positioning arm(s) can be coarse adjusted first, and then fine-adjusted, and the positioning efficiency and accuracy of the lateral canthi can be improved through the above two-step adjustment process.

(4) The area array camera is used to improve the clarity and accuracy of the two-dimensional image taken, provide an accurate data source for subsequent data processing, and thus improve the parameter measurement accuracy of the apparatus.

DRAWING DESCRIPTION

The drawings are used for a better understanding of the invention and do not constitute undue limitation of the invention. Among them:

EXAMPLES

Illustrative embodiments of the invention are described below in conjunction with the attached drawings, which include various details of embodiments of the invention for the purpose of understanding and should be considered to be only illustrative. Therefore, persons of ordinary skill in the art should be aware that various changes and modifications may be made to the embodiments described herein without departing from the scope and spirit of the present invention. Again, for clarity and conciseness, descriptions of known functions and structures have been omitted from the following descriptions.

In order to solve at least one problem in the background techniques, an ocular parameter evaluation apparatus, or an ocular parameter measurement apparatus, is provided according to one or more aspects of an embodiment of the invention.

Figure 1:
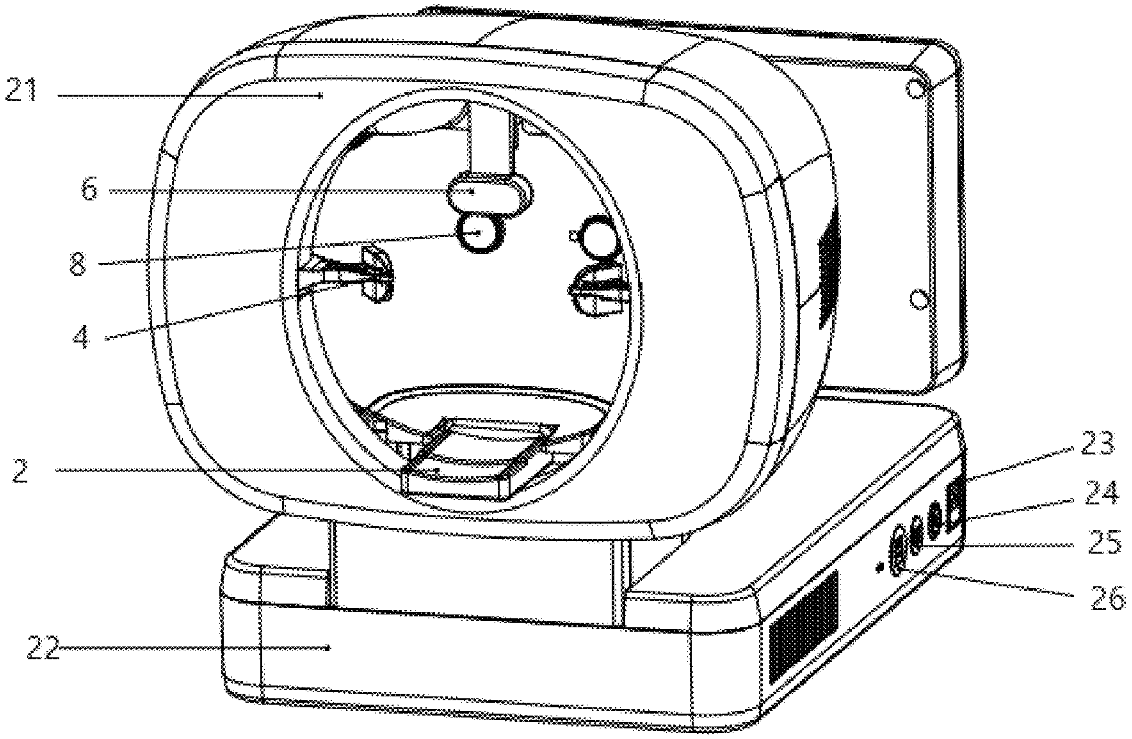
FIG. 1 is an axial-side diagram of an ocular evaluation apparatus according to an embodiment of the invention.
Figure 6:
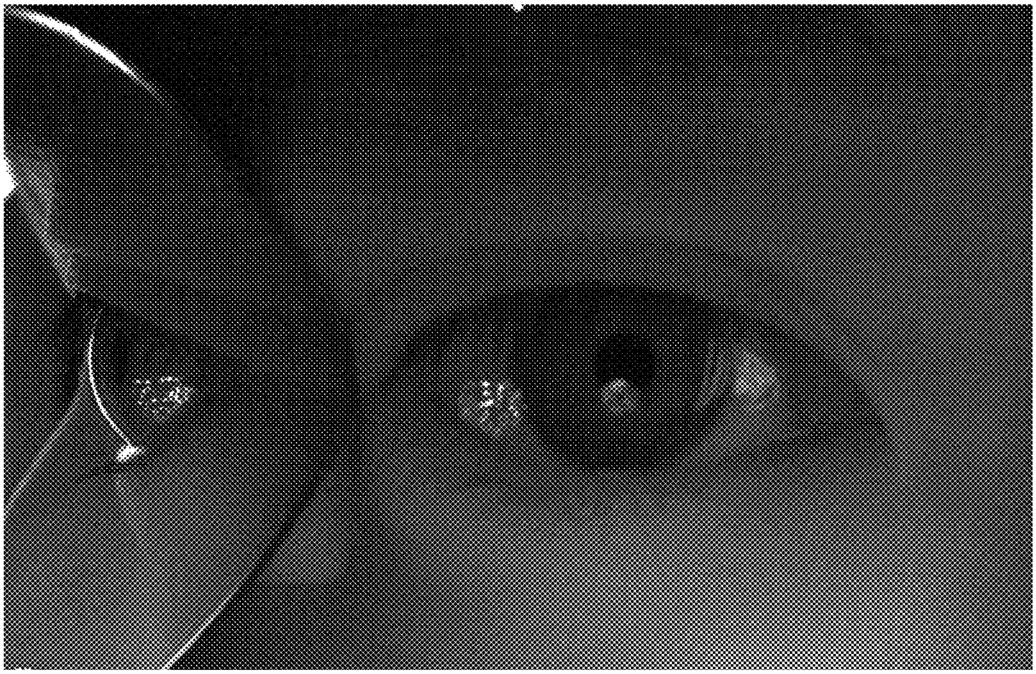
FIG. 6 is an image acquired by an ocular parameter evaluation apparatus according to an embodiment of the invention.

The evaluation apparatus, shown in FIG. 1, comprises a measurement unit and a human-computer interaction unit, both of which are configured on a base. In order to facilitate the use by the operator and the person being measured, the measurement unit and the human-computer interaction unit are distributed on the front and rear sides of the base. When the operator facing the human-computer interaction unit conducts the measurement operation, it can conveniently observe the head attitude of the measured person and control the working state of the equipment. Accordingly, the face of the person being measured faces the housing 21 of the measuring unit. The exemplary human-computer interaction unit may be a combination of a display and a keyboard, or a touch display 17, etc. Further, the measuring unit includes at least one camera module, at least one canthus positioning point and a light source module. The camera module is used to collect eye feature data. The data mentioned here refers to images or video streams that can continuously display the eye. The human-computer interaction unit is controllably connected with the canthal positioning arms to adjust the position of the canthal positioning arms so that the canthal positioning arms are positioned at the lateral canthi of the eyes. As described in the background technology, the accuracy of the measurement results of the equipment in the relevant technology strongly depends on the experience of the user, and the different operating habits between individuals lead to differences in the positioning of the canthal positioning arms outside of the eye, and it is difficult for the operator to accurately locate the left and right outer canthal positioning arms. In order to overcome the above problems, each of the canthal positioning arm(s) of the invention are installed on a displacement platform, and the displacement platform adjusts the canthal positioning arm after receiving an instruction sent by the human-computer interaction unit, so as to accurately locate the canthal positioning arm on the lateral canthus of the eye. Even in the face of the problem of positioning the lateral canthi of the left and right eyes at the same time, it is only necessary to set one canthal positioning arm on each side of the evaluation apparatus. It is understandable that the operator needs to observe the position of the canthal positioning arms in real time when adjusting the position of the canthal positioning arms. The observation can be made in a variety of ways, for example, the distance information between the eye and the canthal positioning arms can be obtained by observing the distance screen between the two points collected continuously. Alternatively, a distance measurement unit may be set on the canthal positioning arms. When the measurement value of the distance measurement unit reaches a set threshold, it indicates that the canthal positioning arms have been successfully positioned with the lateral canthi of the eyes. Further, each canthal positioning arm is connected with a tiltable mirror. The light source comprises a plurality of discrete distributed light bars 13 and a near-infrared light source. The light bars are discretely distributed among each other, and/or the individual luminaries within the light bars are discretely distributed. The near-infrared light source is selectively matched with the light bars to assist the work of the camera module. “Selectively” in this context means that the near-infrared light source is only used in conjunction with the light bars in a specific measurement mode to enable the camera module to obtain high-precision eye data. It is precisely because of the selective cooperation between the near-infrared light source and the light bars that the evaluation apparatus in an embodiment can provide a rich light field condition, thus satisfying the measurement of a variety of parameters, so that the evaluation apparatus can be applied to a variety of measurement modes at a low cost to obtain a wealth of measurement data. The mirror is used to project the virtual image of the eye, so as to facilitate the camera module to obtain a clear image of the eye. In some measurement scenes, the camera module collects the virtual image in the mirror to obtain various features of the eye. Compared with the eye image taken from the front, the tilted mirror can clearly reflect the outer contour of the eyeball surface (such as the raised contour curve) and the detailed features of the eye from the side of the eyeball, especially when illuminated by near-infrared light, providing a clear image of the eyeball surface. At the same time, with the different opening sequence of multiple light bars and the characteristics of the NIR light source, the longest reflected light of the eyeball can be captured, providing accurate measurement data for obtaining the extent of exophthalmos. In addition, the above recording process can obtain the data of a first gaze position image of the eye (facing forward), a second gaze position image (inside, outside, up, down), a third gaze position image (inside up, inside down, outside up, outside down), and a video stream of the eye motion. Moreover, through the above measurement process and the subsequent image data processing, multiple measurement parameters such as ocular exophthalmia, ocular fissure width, ocular motion and conjunctival congestion can be obtained at the same time. The specific measurement process is described below. It can be seen from the above description that the device in the embodiment is simple to operate, and the measurement can be completed simply by taking video or images after positioning the lateral canthi, and various eye parameters can be obtained by subsequent image processing means, which greatly improves the measurement efficiency and accuracy of data measurement. It solves the problems of high measurement cost, low measurement efficiency and inability to measure multiple data synchronously, and the measurement equipment has no side effects such as radiation. In addition, when the NIR light source is turned on, the lighting sequence of the light bars is controlled successively to illuminate the light bars at different positions on the surface of the eyeball, and the camera module is controlled synchronously to collect the virtual eye video stream in the mirror. The human-computer interaction unit intercepts the image frame corresponding to the reflected light with the longest visible light column appearing on the eyeball in the virtual image video stream, and obtains the ocular prominence value by analyzing the data of the intercepted image frame. The near-infrared light source is used in conjunction with the light bars to create the required light field conditions in the eye. The light source setting is very important for the acquisition of image data. In the normal visible light band of 400-700 nm, the color(s) of different parts of the eye, namely the pupil, iris, and sclera, has almost no effect on imaging. Due to the gradual structure of the corneal limbus in the contact part of the iris and sclera, it is impossible to accurately identify the spherical center of the eye. The peak absorption of human melanin pigment occurs at about 335 nm, and it is almost completely non-absorbed for wavelengths over 700 nm, while the reflectivity of iris is quite stable in near-infrared wavelengths over 700 nm. Therefore, the invention adopts a near-infrared light field, which can clearly distinguish the boundaries of the sclera, the iris and the pupil. Then, the pupil center can be accurately identified in subsequent image processing, and the measurement extent of exophthalmos can be improved. In addition, the invention further sequentially activates the light bars in sequence when measuring the degree of exophthalmia. Compared with a point light source, the light emitted by the light bars is strip-shaped with a substantially equal uniform intensity, ensuring that the light intensity reflected by the eyeball is also of substantially uniform intensity. This helps present a clear eye contour in the mirror and facilitates obtaining the center point of the pupil in the subsequent image processing, thereby improving measurement accuracy and stability. Specifically, see FIG. 6, which shows a virtual image captured in a mirror, reflecting that the apparatus of the invention can clearly capture the reflected light of the eye. On the other hand, it is difficult to represent the extent of exophthalmos of the eyeball in the ocular image. More favorable is that compared with traditional measuring equipment, the apparatus of the invention has higher stability of measured data, smaller numerical deviation in multiple measurements, and less data fluctuation. For details, see the comparative data in Table 1. Table 1 shows the statistical results after measuring each of four test subjects 10 times. It can be seen from the data in the table that the apparatus of the invention can obtain stable measurement data for different test subjects, and the standard deviation of the data is small and the stability is high. Therefore, the apparatus of the invention no longer depends on the experience of the instrument user, and can track data changes of the measured person stably for a long time, and the measurement results are very reliable.

TABLE 1

Comparison of measurement results between the apparatus of the invention and instruments in related technologies

| | Apparatus of the invention | | | | Instruments in related technologies | | | |
|---|---|---|---|---|---|---|---|---|
| | Left eye | | Right eye | | Left eye | | Right eye | |
| Subject | Average Value | Standard Gap | Average Value | Standard Gap | Average Value | Standard Gap | Average Value | Standard Gap |
| 1 | 16.66 | 0.13 | 16.65 | 0.09 | 16.00 | 0.32 | 16.70 | 0.46 |
| 2 | 18.56 | 0.17 | 19.05 | 0.12 | 18.55 | 0.35 | 18.95 | 0.47 |
| 3 | 13.56 | 0.18 | 13.20 | 0.15 | 12.80 | 0.51 | 13.35 | 0.32 |
| 4 | 19.26 | 0.23 | 19.95 | 0.10 | 18.50 | 0.50 | 19.50 | 0.50 |

Optionally, the evaluation device also includes a control unit, which obtains instructions received by the human-computer interaction unit to control the movement of the canthal positioning arms and position the canthal positioning arms against the lateral canthi of the eyes. In one embodiment, the control unit is integrated in a base, and the control unit may include multiple sub-control modules to achieve different data processing and control operations. In the embodiment shown in FIG. 3, each sub-control module of the control unit may be configured on a first motherboard 14 and a second motherboard 16, respectively. The control unit is electrically connected with the human-computer interaction unit to receive the control command issued by the operator, and according to the command, control the movement of the canthal positioning arms, and finally accurately position the canthal positioning arms at the lateral canthi of the eyes.

Optionally, the light bars and the near-infrared light source are electrically connected with the control unit, wherein the near-infrared light source selectively cooperates with the light bars, including: the control unit controls the light bars to start in a predetermined order according to the different measurement modes, or controls the near-infrared light source to start, or controls the light bars to start in a predetermined sequence and controls the NIR light source to start. In an optional embodiment, the evaluation device also includes an illuminated light source, which includes but is not limited to an incandescent lamp. As mentioned above, the near-infrared light source is selectively turned on to form different light fields with the light bars to create a light field environment that meets the needs of use for the completion of specific recording tasks. In one embodiment, the following four measurement modes are involved: the measurement mode of eyeball exophthalmia, the measurement mode of eye motion, the measurement mode of eye fissure width, and the measurement mode of conjunctival congestion. The near-infrared light source and light bar(s) should be turned on in the measurement mode of ocular exophthalmia and eye motion. In the conjunctival congestion measurement mode, only the horizontal indicator light and the illuminated light source need to be turned on. The horizontal indicator light means that the light bar(s) controlled by the control unit is lit in a predetermined manner to form an indicator light. For the palpebral fissure width measurement mode, the light source that needs to be turned on varies according to the data post-processing mode selected by the operator. For example, when a dynamic segmentation algorithm is used to process the data, only the illumination light source needs to be turned on to meet the measurement needs of the palpebral fissure width. When a semantic segmentation algorithm is used to process the data, it is only necessary to turn on the near-infrared light source.

Optionally, the camera module is electrically connected with the control unit, where, in response to the opening state of the light bars or near-infrared light source, the control unit controls the camera module to collect the eye video stream in the mirror according to the different measurement modes, or controls the camera module to collect the first gaze position image, second gaze position image and/or third gaze position image, or controls the camera module to collect a video stream of eye motion state(s). In practice, in order to accurately measure various characteristic data of the eye, there are differences in the data collected by the camera module for different measurement modes. Specifically, for the measurement mode of eyeball exophthalmia, after the light source corresponding to the control light source module is turned on, the camera module is controlled to record the video stream of the eye remaining motionless from the mirror on the side of the eye. In the mode of eye motion measurement, it is necessary to control the camera module to record the first gaze position image of the measured person without the light bars on. Then, each light bar is turned on in sequence to take an image of the eye moving along the light bars. When choosing the semantic segmentation algorithm, it is only necessary to open the near-infrared light source and control the camera module to obtain the first gaze position image of the eye in the near-infrared light field. In the measurement mode of conjunctival congestion and palpebral fissure width, when the light source is turned on, it is necessary to control the camera module to capture the video stream of eye rotation along the light bars.

Optionally, the measurement modes are one or more of the modes for measuring extent of exophthalmia, eye motion, eye palpebral fissure width, or conjunctival congestion. It is understood that the technical solution provided in one embodiment is intended to address the problem of equipment in the relevant technology being unable to measure one or more ocular data at a low cost at a time. Accordingly, the measuring apparatus in this embodiment integrates both light bars and a near-infrared light source, and in other embodiments, the measuring device further includes an illuminating light source, such as an incandescent lamp. After the operator selects the corresponding measurement mode, the control unit controls the corresponding light sources to cooperate with each other according to the selected measurement mode, so as to create a light field environment that meets the working requirements of the camera module, and then record the data using the camera module. Specifically, in the ocular exophthalmia measurement mode, after the near-infrared light source is turned on, the light bars are then sequentially illuminated (such as from left to right, or from right to left), and the camera module is controlled to take an image of the left eye or the right eye with the eye looking straight ahead (in this mode, the eye remains stationary). By obtaining the longest reflected light of visible light column appearing on the eyeball in the mirror from the photograph, the image data is analyzed and processed to determine the corneal apex and the pupillary center is determined using a neural network. Then, from the position of the optical center of the unit, the position of the outer canthus point of the eye, the tilt angle of the mirror, the apex of the cornea and the center of the pupil, the exophthalmia is calculated, wherein the tilt angle of the mirror is the angle between the mirror and the imaging surface. In the eye motion measurement mode, after the near-infrared light is turned on, the light bars are controlled to light the indicator light in eight directions (such as the eight directions indicated by the meter azimuth chart), clockwise (or counterclockwise), and the tested person controls the eye movement following the indicator light according to the voice command. The camera module captures the first gaze position image (face in front), the second gaze position image (inside, outside, up and down directions, or the four directions of up, down, left and right in the meter azimuth map), and the third gaze position image (inside up, inside down, outside up and outside down directions) of the measured eye moving to the extreme position in the direction to be measured, or known as the northeast, southeast, northwest, southwest direction in the meter font azimuth map. The first gaze position image (facing forward) is compared with the second gaze position image and the third gaze position image, respectively, and the activity angle of eye motion is calculated. In the dynamic segmentation measurement mode of palpebral fissure width, the light bars are lit successively (from left to right, or from right to left), and the tested person rotates his/her eyes around the tracking point under the instruction of the indicator light. At the same time, the camera module captures the video stream for 20 s. In the later stage, a neural network is used to separate the static and dynamic intersection points from each frame of the video stream, the eyelid contour is obtained through the set of intersection points, and then the upper and lower distance of the eyelid contour on the center line of the pupil is calculated to obtain the palpebral fissure width. In the semantic segmentation measurement mode of palpebral fissure width, the near-infrared light source is turned on first to form a 700-1200 nm near-infrared light field in the recording area. The first gaze position image of the tested person's eyes in the near-infrared light field is captured by the camera module. The background, iris, sclera and pupil are separated from the first gaze position image by the training method of the neural network. Then, the center of the pupil is obtained from the divided pupil, and the center line of the pupil in the vertical direction is obtained. The distance between the intersection of the sclera, iris or pupil and the background on the central line of the pupil can be obtained, then the palpebral fissure width can be obtained. In the conjunctival congestion measurement mode, the tested person rotates their eyes left and right around in response to the tracking point indicated by the indicator light while capturing the video stream. In the later stage, the eye image is obtained by image segmentation of the video stream, and the red channel value and blue channel value of each pixel are extracted from the eye image. The percentage of conjunctival congestion is determined by the ratio of the red channel value to the blue channel value for each pixel.

Optionally, the wavelength of the near-infrared light source is 700-1200 nm. After analyzing the data obtained by the camera module, it can be found that when the visible light wavelength range is 400-700 nm, the color of different parts of the eye, such as the pupil, iris, and sclera, has little effect on imaging. Due to the gradual structure of the corneal limbus where the iris meets the sclera, when the eye is irradiated with light in the visible band, the center of the eye cannot be accurately identified from the recorded data. After many experiments, the inventors found that for wavelengths above 700 nm, the eye absorbs almost none of the light, and the reflectivity of the iris is quite stable in the near-infrared wavelengths above 700 nm. Therefore, the near-infrared light field used in one embodiment can clearly distinguish the sclera, iris, and pupil boundaries, which can better improve the accuracy and stability of the algorithm. Therefore, the wavelength of the NIR light source used in this embodiment is 700-1200 nm, which can significantly improve the measurement accuracy of the extent of exophthalmia, ocular motion, and palpebral fissure width.

Optionally, the evaluation apparatus also comprises a head rest 6 and a jaw rest 2, wherein the head rest is connected with a horizontal moving platform 7, and the control unit is electrically connected with the horizontal moving platform to adjust the front and rear positions of the head rest. The jaw rest is connected with the vertical moving platform 1, and the control unit is electrically connected with the vertical moving platform to adjust the upper and lower positions of the jaw rest. In the embodiment shown in FIG. 3, the head position of the subject can be controlled by setting independent moving platforms for the jaw rest and the head rest, respectively, so that the eye of the subject is initially aligned with the canthus positioning arm. Then, through the moving platform of the canthus positioning arm, such as the left displacement platform 3 or the right displacement platform 12, the position of the canthus positioning arm is further adjusted to accurately locate the lateral canthi of the eyes. Through the above two-step adjustment process, the localization efficiency and accuracy of lateral canthi positioning can be improved.

Figure 2:
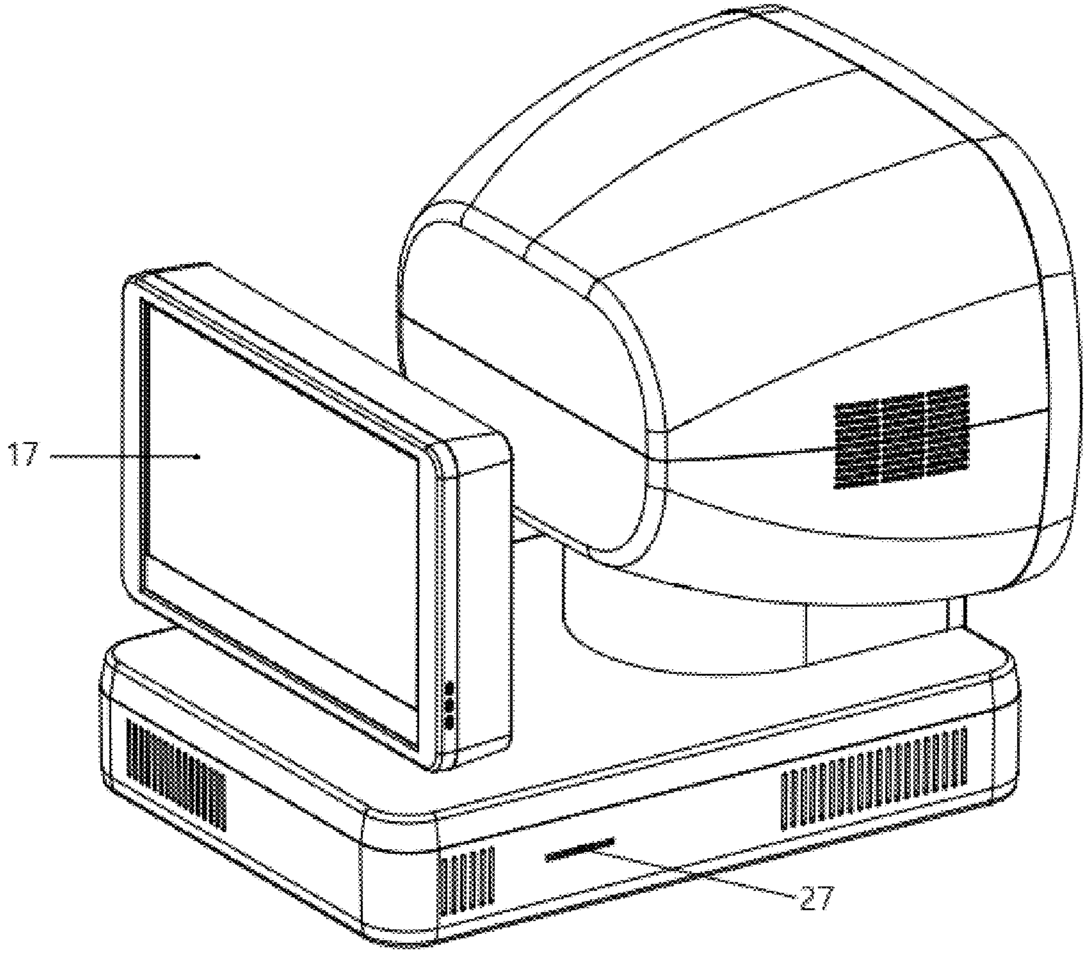
FIG. 2 is a schematic of another perspective of an ocular parameter evaluation apparatus according to an embodiment of the invention.
Figure 3:
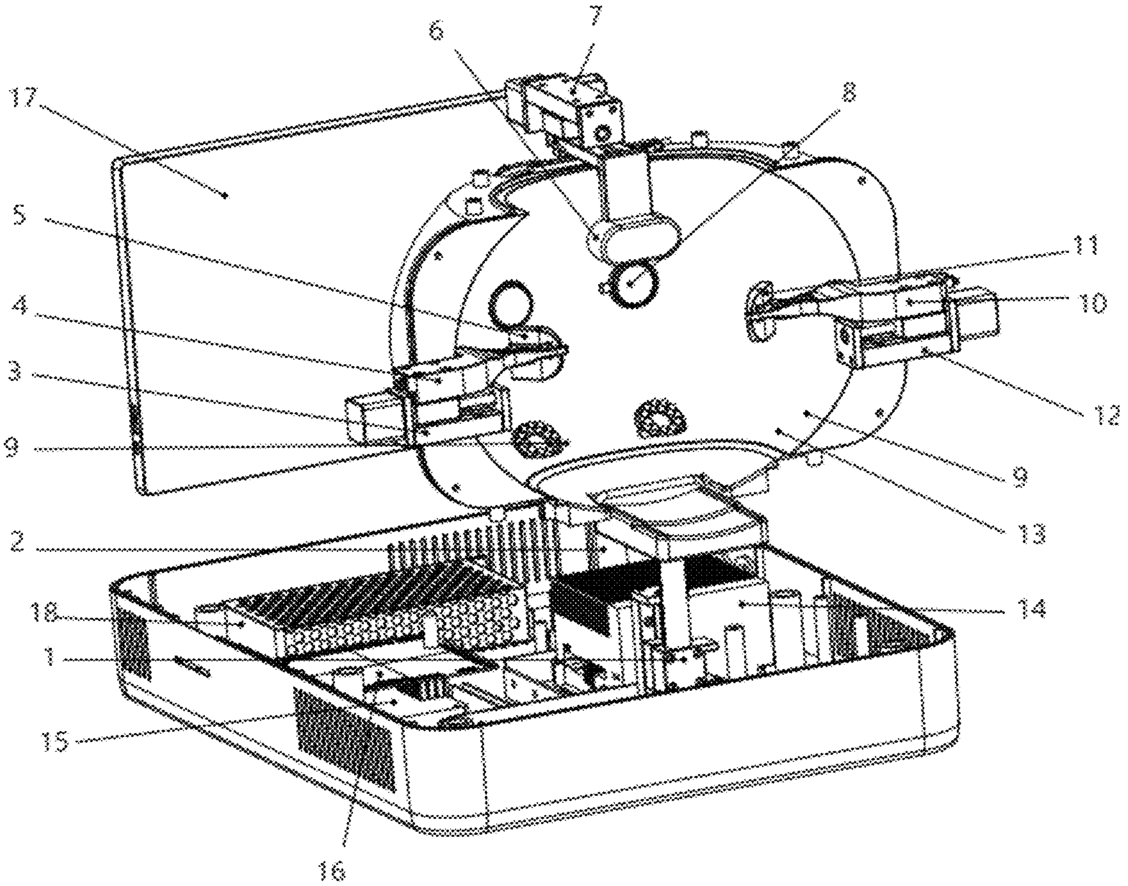
FIG. 3 is a schematic of a local structure of an ocular parameter evaluation apparatus according to an embodiment of the invention.
Figure 4:
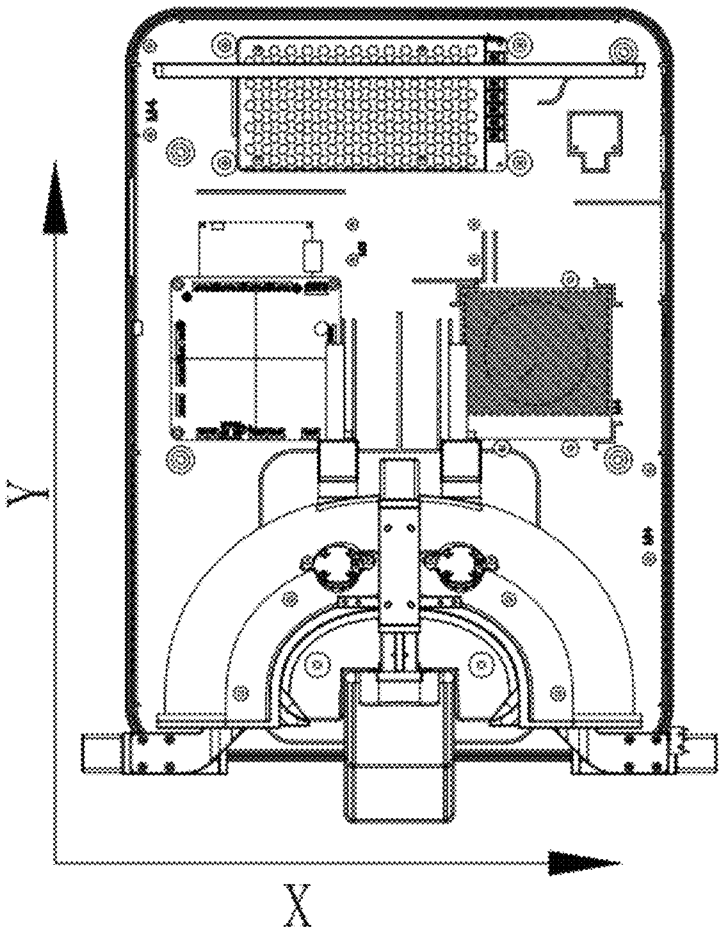
FIG. 4 is a top view of a local structure of an ocular parameter evaluation apparatus according to an embodiment of the invention.
Figure 5:
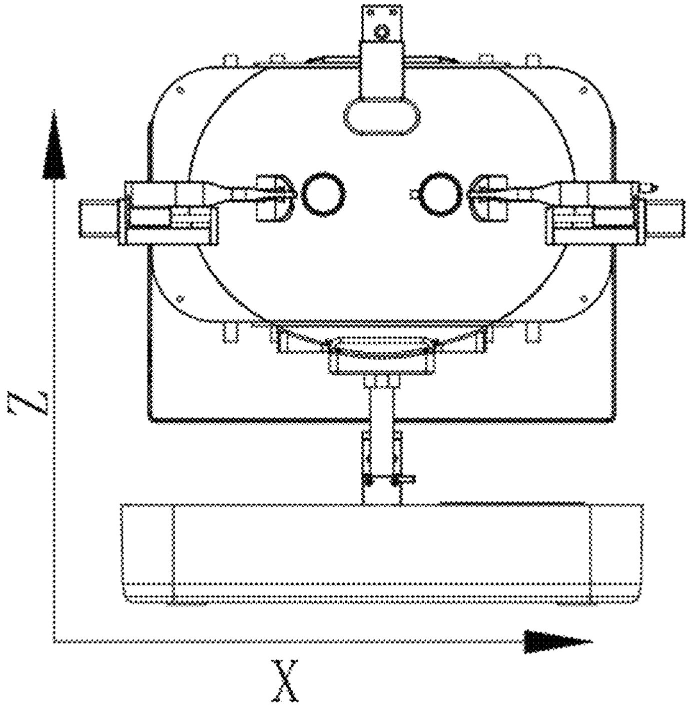
FIG. 5 is a front view of a local structure of an ocular parameter evaluation apparatus according to an embodiment of the invention.

Optionally, the number of the canthus positioning arms and the mirrors are both two, and are respectively distributed on the left and right sides of the measuring unit. In the embodiment shown in FIGS. 1 to 3, the canthus positioning arms includes the left canthal positioning arm 4 and the right canthal positioning arm 10, and the mirrors also include two pieces, respectively, the left mirror 5 and the right mirror 11. The components are arranged on the left and right sides of the measuring unit, making it possible to measure both eyes of the subject simultaneously. The mirror is configured to tilt on the canthal positioning arm to form a virtual image corresponding to the eye in the mirror. As shown in FIG. 3, the two mirrors are tilted to the outside of the human face axis, so that the reflection of the mirror faces the camera module so that the camera module can capture the virtual image in the mirror.

Optionally, the camera module comprises left and right settings for two area array cameras 8, and/or the number of near-infrared light sources 9 is two and they are distributed on both sides of the measuring unit. The above camera and near-infrared light sources are set into two groups respectively, and the two groups correspond to one eye respectively, which can provide sufficient light for the eye to be measured, and thus improve the recording effect of the corresponding eye. It should be noted that in one embodiment, the recorded data is post-processed to obtain various required measurement results, so the accuracy of the measurement results is closely related to the accuracy of the recorded data. For this purpose, an area array camera is used in one embodiment to improve the clarity and accuracy of the two-dimensional images taken.

Optionally, the base 22 has a card slot 27 and/or multiple types of communication interfaces. As shown in FIGS. 1 and 2, the card slots include, but are not limited to, slots for inserting a security/identification card. The card slot is electrically connected with a card reading module 15 in the base. Accordingly, communication interfaces include, but are not limited to network access entry 26, a USB interface 25, etc. Of course, in order to facilitate the operation of the apparatus, the corresponding power switch 24 and power interface 23 are configured on the same side of the communication interface. The power interface is connected to a power supply 18. It is understood that other types of I/O interfaces can also be integrated on the base of the apparatus, to connect input devices like a keyboard, a mouse, etc.; to connect output devices such as a cathode ray tube (CRT), a liquid crystal display (LCD), speakers, etc.; to connect a storage device like a hard disk, etc.; and to connect communication devices like network interface cards such as a LAN card, a modem, etc. The communication portion performs communication processing over a network such as the Internet. The drive is also connected to the I/O interface as needed. Detachable media, such as disks, optical disks, magnetic discs, semiconductor memory, etc., are mounted on the drive as required so that computer programs read from it can be mounted into the storage section as required.

The above specific embodiments do not constitute limitations on the scope of protection of the invention. It should be understood by those skilled in the art that, depending on design requirements and other factors, a wide variety of modifications, combinations, subcombinations, and substitutions can occur. Any modification, equivalent replacement and improvement made within the spirit and principles of the invention shall be included in the scope of protection of the invention.

What is claimed is:

1. An ocular parameter evaluation apparatus, comprising:

a measurement unit and a human-computer interaction unit, wherein:

the measurement unit and the human-computer interaction unit are on a base;

the measurement unit comprises at least one camera module, at least one canthal positioning arm, and a light source module, wherein the camera module is configured to collect data of one or more eyes;

the human-computer interaction unit adjusts a position of the at least one canthal positioning arm, so that the at least one canthal positioning arm is localized at a lateral canthus of the one or more eyes;

the at least one canthal positioning arm is connected to an obliquely-arranged mirror;

the light source module comprises a plurality of light bars discretely distributed and a near-infrared light source;

the near-infrared light source is selectively coordinated with the plurality of light bars to assist the camera module in operation;

after the near-infrared light source is turned on, the plurality of light bars are controlled successively to illuminate different positions on a surface of the one or more eyes, and the camera module is synchronously controlled to collect a virtual image video stream of the one or more eyes in the mirror; and the human-computer interaction unit intercepts an image frame corresponding to reflected light with a longest visible light column appearing on the one or more eyes in the virtual eye video stream, and obtains an ocular prominence value by analyzing data of the intercepted image frame.

2. The ocular parameter evaluation apparatus in claim 1, further comprising a control unit that obtains an instruction received by the human-computer interaction unit to control movement of the at least one canthal positioning arm and position the at least one canthal positioning arm against the lateral canthus of the one or more eyes.

3. The ocular parameter evaluation apparatus in claim 2, wherein:

the plurality of light bars and the near-infrared light source are electrically connected with the control unit, and the near-infrared light source is selectively coordinated with the plurality of light bars, such that the control unit controls the plurality of light bars to start in a predetermined order according to different measurement modes, or controls a start of the near-infrared light source, or controls the plurality of light bars to start in a predetermined sequence and controls the near-infrared light source to start.

4. The ocular parameter evaluation apparatus in claim 3, wherein the camera module is electrically connected to the control unit.

5. The ocular parameter evaluation apparatus in claim 4, wherein in response to an opening state of the plurality of light bars or near-infrared light source, the control unit controls the camera module to collect the virtual eye video stream in the mirror according to the different measurement modes.

6. The ocular parameter evaluation apparatus in claim 4, wherein in response to an opening state of the plurality of light bars or near-infrared light source, the control unit controls the camera module to collect a first gaze position image, a second gaze position image and/or a third gaze position image.

7. The ocular parameter evaluation apparatus in claim 3, wherein the different measurement modes are at least one of the following: eyeball exophthalmia, eye motion, palpebral fissure width, and conjunctival congestion.

8. The ocular parameter evaluation apparatus in claim 7, wherein the different measurement modes include at least two of the different measurement modes.

9. The ocular parameter evaluation apparatus in claim 2, further comprising a head rest connected with a horizontal moving platform, and a jaw rest connected with a vertical moving platform.

10. The ocular parameter evaluation apparatus in claim 9, wherein the control unit is electrically connected with the horizontal moving platform to adjust a front-and-back position of the head rest, and the control unit is electrically connected with the vertical moving platform to adjust an up-and-down position of the jaw rest.

11. The ocular parameter evaluation apparatus in claim 1, wherein the near-infrared light source has a wavelength of 700-1200 nm.

12. The ocular parameter evaluation apparatus in claim 1, comprising:

two canthal positioning arms and two mirrors, respectively configured on left and right sides of the measurement unit;

wherein the two mirrors are configured to tilt on the two canthal positioning arms to form a virtual image corresponding to the eye in the corresponding mirror.

13. The ocular parameter evaluation apparatus in claim 1, wherein the camera module comprises two area array cameras configured at left and right sides of the camera module.

14. The ocular parameter evaluation apparatus in claim 1, comprising two near-infrared light sources distributed on sides of the measurement unit.

15. The ocular parameter evaluation apparatus in claim 1, wherein the base has a card slot.

16. The ocular parameter evaluation apparatus in claim 15, wherein the base has a plurality of communication interfaces.

17. The ocular parameter evaluation apparatus in claim 1, wherein the base has a plurality of communication interfaces.

* * * * *